United States Patent
Lee et al.

(10) Patent No.: US 9,452,983 B2
(45) Date of Patent: Sep. 27, 2016

(54) METHOD FOR REFINING QUINOLINIC ACID

(71) Applicant: CJ CHEILJEDANG CORP., Seoul (KR)

(72) Inventors: In Sung Lee, Seoul (KR); Jae Hun Yu, Seoul (KR); Ju Un Park, Osan-si (KR); Chong Ho Lee, Seoul (KR); Hideki Murata, Seoul (KR)

(73) Assignee: CJ CHEILJEDANG CORP. (KR)

( * ) Notice: Subject to any disclaimer, the term of this patent is extended or adjusted under 35 U.S.C. 154(b) by 0 days.

(21) Appl. No.: 14/779,886

(22) PCT Filed: Mar. 6, 2014

(86) PCT No.: PCT/KR2014/001833
§ 371 (c)(1),
(2) Date: Sep. 24, 2015

(87) PCT Pub. No.: WO2014/163301
PCT Pub. Date: Oct. 9, 2014

(65) Prior Publication Data
US 2016/0052885 A1  Feb. 25, 2016

(30) Foreign Application Priority Data
Apr. 1, 2013 (KR) .................. 10-2013-0035462

(51) Int. Cl.
*C07D 213/80* (2006.01)
*C07D 213/803* (2006.01)

(52) U.S. Cl.
CPC ......... *C07D 213/803* (2013.01); *C07D 213/80* (2013.01)

(58) Field of Classification Search
None
See application file for complete search history.

(56) References Cited

U.S. PATENT DOCUMENTS 4,537,971 A    8/1985  Rebhahn et al.
2014/0315263 A1  10/2014  Kim et al.

FOREIGN PATENT DOCUMENTS

KR    101223904    1/2013

OTHER PUBLICATIONS

A. Uchida et al., "Regioselective hydroxylation of quinolinic acid, lutidinic acid and isocinchomeronic acid by resting cells of pyridine dicarboxylic acid-degrading microorganisms", Appl Microbiol Biotechnol, (2003), vol. 62, pp. 337-341.
International Search Report—PCT/KR2014/001833 dated May 30, 2014.
Written Opinion—PCT/KR2014/001833 dated May 30, 2014.

*Primary Examiner* — Zinna Northington Davis
(74) *Attorney, Agent, or Firm* — Cantor Colburn LLP (57) ABSTRACT

Provided is a method for refining quinolinic acid, including the steps of: preparing a fermentation solution including at least one of quinolinic acid and a salt thereof; removing microbial cells from the fermentation solution; preparing an acidic composition containing at least one of quinolinic acid and a salt thereof at a saturation concentration or more by adding an acid to the fermentation solution; and recovering a crystal of least one of quinolinic acid and a salt thereof from the acidic composition.

19 Claims, 3 Drawing Sheets

METHOD FOR REFINING QUINOLINIC ACID

TECHNICAL FIELD

The present invention relates to a method of refining quinolinic acid.

BACKGROUND ART

Quinolinic acid is a compound that is widely used as an intermediate for medicines, dyes, agricultural pesticides, and the like. In general, quinolinic acid is chemically prepared from a starting material such as quinoline, 2,3-dimethylpyridine, or 8-hydroxyquinoline obtained in petrochemical processes. For example, a chemical synthesis method of quinolinic acid includes obtaining a copper salt of quinolinic acid from a sulfate such as copper sulfate; and removing copper ions from the copper salt in a form of copper oxide precipitate. In such a synthesis method of quinolinic acid, the additional process of removing copper from copper salt of quinolinic acid may lead to generation of a large amount of byproducts and a low yield. The synthesis method may also result in a large amount of impurities, and thus, it may also be difficult to obtain quinolinic acid with a high yield with the synthesis method, even by recirculating a mother solution resulting from separation of crystals of quinolinic acid.

In recent times, there has been research into methods of producing quinolinic acid through a fermentation process. Producing quinolinic acid through a fermentation process is simple and results in a small amount of byproducts. However, a fermentation solution resulting from the fermentation process may include, in general, a low concentration of quinolinic acid, which is present as a combination with a salt.

Therefore, there is a need for an economical refining method for obtaining high-purity quinolinic acid crystals from the fermentation solution with a high recovery rate and low costs.

DETAILED DESCRIPTION OF THE INVENTION

Technical Problem

The present invention provides a novel, economical method of purifying quinolinic acid from a fermentation solution.

Technical Solution

According to an aspect of the present invention, there is provided a method of refining quinolinic acid, the method including: preparing a fermentation solution including at least one of quinolinic acid and a salt thereof; removing microbial cells from the fermentation solution; preparing an acidic composition including the at least one of quinolinic acid and a salt thereof at a saturation concentration or more by adding an acid to the fermentation solution from which the microbial cells were removed; and recovering crystals of the at least one of quinolinic acid and a salt thereof from the acidic composition.

According to one or more embodiments, quinolinic acid may be refined through a relatively simple process via adding an acid to a fermentation solution including quinolinic acid. High-purity quinolinic acid may be obtained with a high yield by recirculating a mother solution resulting from crystal separation following acid treatment.

BEST MODE

Hereinafter, exemplary embodiments of a method of refining quinolinic acid will be described in greater detail.

According to an embodiment of the present disclosure, a method of refining quinolinic acid includes: preparing a fermentation solution including at least one of quinolinic acid and a salt thereof; removing microbial cells from the fermentation solution; preparing an acidic composition including the at least one of quinolinic acid and a salt thereof at a saturation concentration or more by adding an acid to the fermentation solution from which the microbial cells were removed; and recovering a crystal of the at least one of quinolinic acid and a salt thereof from the acidic composition.

According to the refining method, high-purity quinolinic acid may be obtained with a high yield through simple processes by adding an acid to the fermentation solution including a salt of quinolinic acid to form a crystal of quinolinic acid and then recovering the crystal of quinolinic acid. Since the acidic composition includes at least one of quinolinic acid and a salt thereof at a saturation concentration or more, at least part of the at least one of quinolinic acid and a salt thereof may be precipitated as crystals.

The fermentation solution used in the refining method may be a fermentation solution cultured with a modified microorganism able to produce quinolinic acid. Types of microorganisms available to prepare the fermentation solution are not specifically limited, and may include any microorganism able to produce quinolinic acid available in the art. For example, the microorganism available in the refining method may be a microorganism belonging to the genus *Escherichia, Enterobacter, Erwinia, Klebsiella, Pantoea, Serratia, Corynebacterium,* and the like.

In some embodiments, the fermentation solution may further include, in addition to quinolinic acid: an organic acid, such as lactic acid, succinic acid, formic acid, or acetic acid; cations such as $Na^+$, $Mg^{2+}$, $NH_4^+$, and $K^+$; anions such as $CO_3^{2-}$, $PO_4^-$, and $SO_4^{2-}$; amino acids such as valine, arginine, and methionine; an non-consumable carbon source, an microorganism available for fermentation having the ability to produce quinolinic acid, and the like.

The acidic composition in the refining method refers to a composition at a pH less than 7 obtained by adding an acid to the fermentation solution and includes the fermentation solution.

The acidic composition in the refining method may have a pH of about 3.5 or less. When the pH of the acidic composition is controlled to be about 3.5 or less, the solubility of quinolinic acid and/or a salt thereof may be reduced so that crystals of quinolinic acid and/or a salt thereof may be precipitated. For example, the acidic composition may have a pH of 3.0 or less, and in some embodiments, a pH of about 2.5 or less, and in some other embodiments, a pH from about 1.0 to about 2.5.

The fermentation solution before the adding of an acid may have a pH of about 4 to about 9. When the fermentation solution before the adding of an acid has a pH within this range, the quinolinic acid may bind to cations such as $Na^+$, $Mg^{2+}$, $NH_4^+$, $K^+$, and the like contained in a culture medium and consequentially be present as a salt thereof such as sodium quinolinate, magnesium quinolinate, ammonium quinolinate, or potassium, having a comparative high solubility of about 100g/L or higher in water. When the fermentation solution has a high pH, precipitated crystals of quinolinic acid may be mixed with crystals of quinolinate. Accordingly, the acidic composition having a pH of pH 3.5 or less may be prepared by adding an acid to the fermentation solution.

In some embodiments of the refining method, in the preparing of the acidic composition, the acidic composition may have a temperature of about 60° C. or less, and in some embodiments, about 50° C. or less, and in some other embodiments, about 40° C. or less, and in some other embodiments, about 0° C. to about 40° C. When the temperature of the acidic composition is within these ranges, the crystals of quinolinic acid may be obtained with improved yield.

In some embodiments of the refining method, the acid added to the culture medium may include at least one selected from sulfuric acid, hydrochloric acid, nitric acid bromic acid (HBr), phosphoric acid ($H_3PO_4$), perchloric acid ($HClO_4$), and a mixture thereof, but is not limited thereto. Any acid available in the art to adjust pH of culture medium may be used. The concentration of the added acid is also not specifically limited.

The refining method may include removing microbial cells from the fermentation solution before the preparing of the acidic composition.

The removing of microbial cells may be performed, but not limited to, using a centrifuge, a filter press, a diatomaceous earth filter, a rotary vacuum filter, or a membrane separator, or by adding a coagulating agent, a floating agent, or the like. Any method available in the art to separate microbial cells may be used.

The fermentation solution conventionally may have a pH of about 4 to about 9. In some embodiments of the refining method, the pH of the fermentation solution may be reduced by adding an acid to agglomerate microbial cells to be effectively removed. The pH of the fermentation solution at which the microbial cells may agglomerate to be effectively removed may be in a range of from about 3 to about 7, and in some embodiments, about 3.5 to about 6.0. However, the pH of the fermentation solution is not limited thereto, and may be in a range in which agglomeration of microbial cells occurs by addition of an acid. For example, the acid added to the fermentation solution may be sulfuric acid, hydrochloric acid, nitric acid, or a mixture thereof, but is not limited thereto. Any acid available in the art to adjust the pH of the fermentation solution may be used. The microbial cells that are removed from the fermentation solution may be dried for use as animal feed or fertilizer.

In some embodiments, the refining method may further include, before the preparing of the acidic composition, removing impurities from the fermentation solution. The purity of quinolinic acid may be improved by the removal of impurities.

The removing of impurities from the fermentation solution may include adding a filtering agent to the fermentation solution to remove impurities and/or insoluble materials.

The filtering agent may be, for example, activated carbon, diamaceous earth, bentonate, acidic terra alba, talc, or the like, but is not limited thereto. Any filtering agent available in the art may be used. The filtering agent to which impurities and insoluble materials are adsorbed may be removed from the fermentation solution by using a filter. For examples, the impurities may include a metal ion. The insoluble materials may include, for example, microbial cells.

In some embodiments, the refining method may further include, before the preparing of the acidic composition, concentrating the fermentation solution. The yield of crystals of quinolinic acid may be increased by the further concentrating of the fermentation solution. The concentrating of the fermentation solution may include removing water to increase the concentration of quinolinic acid in the fermentation solution, and consequently increase the amount of precipitated crystals of quinolinic acid in a subsequent step.

In some embodiments, the refining method may further include, after the preparing of the acidic composition, concentrating the acidic composition. The concentrating of the acidic solution may include removing water used as a solvent to increase the concentration of quinolinic acid in the acidic composition, and consequentially increase the amount of precipitated crystals of quinolinic acid. The crystals resulting from the concentrating of the acidic composition are concentrated crystals of quinolinic acid.

A recovery rate of quinolinic acid crystals may be improved by the removal of the solvent in the concentrating of the acidic composition. For example, a concentration of quinolinic acid concentrated in the concentrating step may be from about 50 g/L to about 400 g/L, and in some embodiments, about 80 g/L to about 300 g/L.

The concentrating of the acidic solution may be performed using, but not limited to, a condenser selected from the group consisting of a centrifugal concentrator, an evaporative condenser, a convection circulation concentrator, a low-temperature vacuum evaporator, a rotary evaporator, a reduced pressure evaporator, a thin-film evaporator, and a plate evaporator. Any concentrator available in the art may be used.

The concentrating of the acidic solution may be performed using a low-temperature vacuum evaporator. For example, a pressure of the low-temperature vacuum evaporator may be in a range of about 10 mmHg to about 760 mmHg, and in some embodiments, about 70 mmHg to about 200 mmHg. For example, a temperature of the low-temperature vacuum evaporator may be in a range of about 10° C. to about 100° C., and in some embodiments, about 40° C. to about 100° C.

In some embodiments, the refining method may further include, after the preparing of the acidic composition, cooling the acidic composition. The yield of quinolinic acid crystals may be increased by the further cooling of the acidic composition. The further cooling of the acidic composition may reduce the solubility of quinolinic acid, and consequentially increase the amount of precipitated crystals of quinolinic acid. The crystals resulting from the cooling are cooled crystals of quinolinic acid.

The cooling of the acidic composition may be performed by natural cooling or controlled cooling. The controlled cooling may be performed at a cooling rate of about 0.01° C./min to about 5° C./min. The lower the cooling temperature, the higher the yield of crystals may become, but the lower the purity of precipitated crystals may become. Accordingly, the cooling temperature may be appropriately controlled in consideration of the yield and purity of precipitated crystals. For example, the cooling temperature may be in a range of about 0° C. to about 40° C., and in some embodiments, about 2° C. to about 30° C.

In some embodiments, the refining method may further include, after the preparing of the acidic composition, adding a quinolinic acid crystal seed to the acidic composition. Precipitation of quinolinic acid crystals may be accelerated by the addition of the quinolinic acid crystal seed. The adding of the quinolinic acid crystal seed may stimulate generation and growth of quinolinic acid crystals, and thus increase the size and purity of recovered crystals of quinolinic acid.

In some embodiments, the refining method may further include, after the recovering of the crystals, recrystallizing the recovered crystals. The purity of recovered crystals may be further improved by the recrystallization of the recovered crystals.

In some embodiments of the refining method, the recovering of the crystals may include separating the crystals from the acidic composition.

The separating of the crystals from the acidic composition is separating precipitated crystals from the acidic composition. The separating of precipitated crystals may be performed using any common separation method available in the art, not limited to a specific method. For example, the separating of precipitated crystals may be performed using a filtration device, such as a filter.

The separated crystals may be readily used in the recrystalling process without additional treatment.

In some embodiments of the refining method, the recovering of the crystals may further include cleaning and drying the separated crystals. In the cleaning and drying of the separated crystals, the cleaning of the separated crystals may be performed using water or a cleaning solution such as an aqueous quinolinic acid solution. Impurities adhered to the crystals of quinolinic acid may be removed by the cleaning of the separated crystals. When an excessive amount of the cleaning solution is used in the cleaning, the yield of the crystals may be reduced. Accordingly, the amount of the cleaning solution used in the cleaning of the crystals may be about 100% or less of a total weight of the separated crystals. For example, the amount of the cleaning solution used in the cleaning of the crystals may be about 50% or less, and in some embodiments, about 20% or less, and in some other embodiments, about 10% or less, based on the total weight of the separated crystals.

In the cleaning and drying of the separated crystals, the drying of the separated crystals may be performed using, but not limited to, common atmospheric or reduced-pressure drying. Any drying method available in the art may be used.

In some embodiments, all or some of a mother solution, obtained from the recovering of crystals, can be recirculated into the fermentation solution. The mother solution resulting from the separating of precipitated crystals in the recovering of the crystals is an acidic solution containing an acid. The acid in the mother solution may be reused by the recirculating of the mother solution. Accordingly, the yield of crystals of quinolinic acid may be improved through the recirculating step.

In some embodiments of the refining method, the yield of crystals of quinolinic acid obtained by the refining method may be about 50% or greater. For example, the yield of crystals of quinolinic acid obtained by the refining method may be about 60% or greater, and in some embodiments, about 70% or greater, and in some other embodiments, about 80% or greater, and in still other embodiments, about 90% or greater, and in yet other embodiments, about 95% or greater, and in still yet other embodiments, about 99% or greater.

Figure 2:
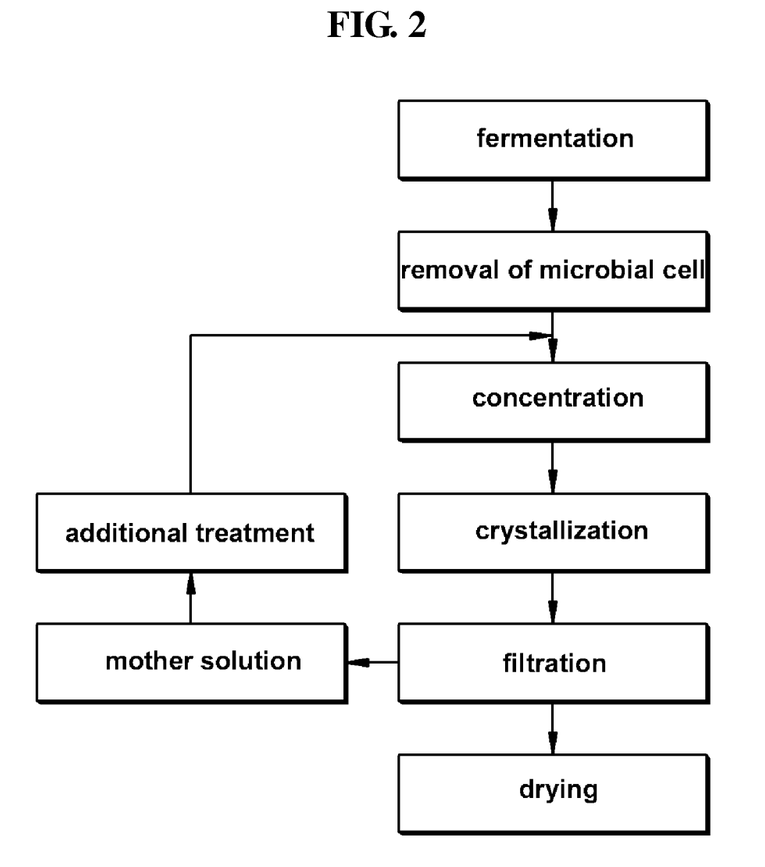
FIG. 2 is a flowchart of a method of refining quinolinic acid, according to an exemplary embodiment, including no recrystallization step.

A method of refining quinolinic acid, according to an exemplary embodiment, will be described with reference to FIG. 2. Referring to FIG. 2, after removing microbial cells from a fermentation solution, the resulting fermentation solution may be concentrated. An acid may be added to the concentrated fermentation solution to obtain an acidic composition, followed by crystallizing quinolinic acid. After filtering precipitated crystals of quinolinic acid, cleaning and drying may be performed to yield crystals of quinolinic acid. A mother solution resulting from the separating of crystals of quinolinic acid may undergo an additional treatment, and then be added back to the fermentation solution from which microbial cells were removed.

In some embodiments, the refining method may further include, after the recovering of the crystals, recrystallizing the recovered crystals. The yield of the recovered crystals may be further improved by the recrystallization.

In some embodiments, the recrystallizing of the recovered crystals may include: dissolving the recovered crystals in a basic solution; preparing an acidic composition including at least one of quinolinic acid and a salt thereof at a saturation concentration by adding an acid to the basic solution; and recovering crystals of the at least one of quinolinic acid and a salt thereof from the acidic composition.

In the dissolving of the recovered crystals in a basic solution, the recovered crystals may be fully dissolved in the basic solution. Quinolinic acid may be completely dissolved in the form of ions in the basic solution. The basic solution may include at least one selected from the group consisting of calcium hydroxide, magnesium hydroxide, calcium carbonate, ammonium hydroxide, sodium hydroxide, barium hydroxide, magnesium carbonate, and a mixture thereof, but is not limited thereto. Any base available in the art may be used. A concentration of the basic solution is not specifically limited provided that it is within a range of fully dissolving about 30 g/L to about 400 g/L of quinolinic acid and maintaining a pH of the basic solution at about 3.5 to about 8.0. For example, the basic solution may include a base in an amount that is equivalent to about 0.1 to about 5 times of moles of quinolinic acid. In the dissolving of the recovered crystals in a basic solution, the temperature of the basic solution may be increased to improve the solubility of the recovered crystals. For example, the temperature of the basic solution may be less than about 100° C., and in some embodiments, about 80° C. or less, and in some other embodiments, about 60° C. or less.

The preparing of the acidic composition including at least one of quinolinic acid and a salt thereof at a saturation concentration by adding an acid to the basic solution is the same as the preparing of an acidic composition by adding an acid to the fermentation solution, except that an acid is added to the basic solution, instead of the fermentation solution. The purity of the crystals may be improved by the recrystallization using the basic solution including the recovered crystals, instead of the fermentation solution.

For example, an acidic composition having a pH of about 3.5 or less, for example, about 1.5 to about 2.5, at which the solubility of quinolinic acid is rapidly reduced may be prepared by adding an acid to the basic solution. The acid may be sulfuric acid, hydrochloric acid, nitric acid, or a mixture thereof, but is not limited thereto. Any acid available in the art may be used. A temperature of the basic solution is not specifically limited, and may be in a range of about 0° C. to about 60° C. to improve the yield of the recrystallized crystals. For example, the temperature of the basic solution may be in a range of about 0° C. to about 40° C.

To further improve the yield of the recrystallized crystals, the acidic composition having a pH of about 3.5 or less may be further concentrated, or the temperature of the acidic composition may be further reduced, thus to increase the amount of the crystals.

To improve the purity of the recrystallized crystals, the refining method may further include removing impurities from the basic solution before the preparing of the acidic composition. The purity of refined quinolinic acid may be further improved by the removal of impurities. Impurities and/or insoluble materials may be removed by adding a filtering agent to the basic solution. The filtering agent may be, for example, activated carbon, diamaceous earth, bentonate, acidic terra alba, talc, or the like, but is not limited thereto. Any filtering agent available in the art may be used. The filtering agent to which impurities or insoluble materials are adsorbed may be removed from the basic solution by using a filter. For examples, the impurities may include a metal ion. The insoluble material may include, for example, microbial cells.

In some embodiments, the recovering of the crystals of the at least one of quinolinic acid and a salt thereof may include separating the crystals from the acidic composition.

The method of refining quinolinic acid may be terminated by the separating of the crystals without additional treatment.

In some embodiments, in the recrystallizing of the recovered crystals, the recovering of the crystals may further include cleaning and drying the separated crystals.

The separating of the crystals from the acidic composition and the cleaning and drying of the separated crystals may be the same as the above described steps of separating, cleaning and drying in the recovering of the crystals of at least one of quinolinic acid and a salt thereof, except that the recrystallized crystals, instead of the primary crystals, are separated, cleaned, and dried. The recovering of the recrystallized crystals, not the primary crystals, may improve the purity of the crystals.

In some embodiments, all or some of a mother solution obtained from the recovering of the crystals, can be recirculated into the fermentation solution. The mother solution resulting from the separating of precipitated crystals in the recovering of the recrystallized crystals is an acidic solution containing an acid. The acid in the mother solution may be reused by the recirculating of the mother solution. Accordingly, the yield of crystals of quinolinic acid may be improved through the recirculating step.

In the refining method including the recrystallizing step, the resulting crystals of quinolinic acid may have a purity of about 90% or greater, and in some embodiments, about 95% or greater, and in some other embodiments, about 98% or greater, and in still other embodiments, about 99% or greater, and in yet other embodiments, about 99.2% or greater.

A method of refining quinolinic acid, according to another exemplary embodiment, will be described with reference to FIG. 3.

Figure 3:
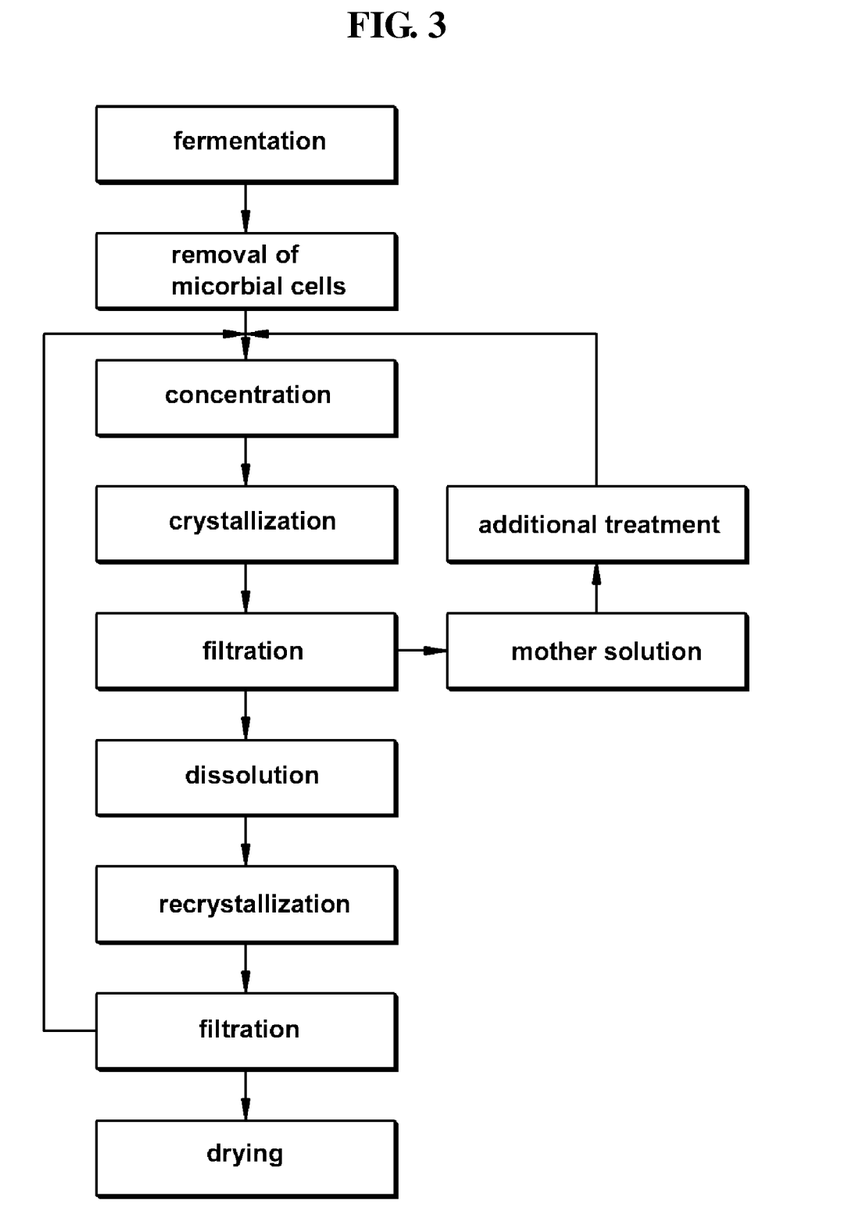
FIG. 3 is a flowchart of a method of refining quinolinic acid, according to another exemplary embodiment, including a crystallization step.

Referring to FIG. 3, after removing microbial cells from a fermentation solution, the resulting fermentation solution may be concentrated. An acid may be added to the concentrated fermentation solution to obtain an acidic composition, followed by crystallizing quinolinic acid. After filtering precipitated crystals of quinolinic acid, cleaning and drying may be performed to yield crystals of quinolinic acid. After completely dissolving the crystals of quinolinic acid in a basic solution, an acid may be added to the basic solution to obtain an acid composition and recrystallize quinolinic acid. The recrystallized quinolinic acid may separated by filtering, followed by cleaning and drying to yield crystals of quinolinic acid. A mother solution resulting from the separating of crystals of quinolinic acid may undergo an additional treatment, and then be added back to the fermentation solution from which microbial cells were removed.

MODE OF THE INVENTION

One or more embodiments of the present disclosure will now be described in detail with reference to the following examples. However, these examples are only for illustrative purposes and are not intended to limit the scope of the one or more embodiments of the present disclosure.

(Refining of Quinolinic Acid)

Example 1

(Fermentation Solution Preparation Step)

A first fermentation solution was prepared by the CJ Cheil Jedang Bioscience R&D center. The prepared first fermentation solution included about 3.75 wt % of quinolinic acid, about 0.52 wt % of organic acids (lactic acid, succinic acid, formic acid, acetic acid, etc.), about 1.25 wt % of ions (cations such as $Na^+$, $Mg^{2+}$, $NH^{4+}$, and $K^+$, and anions such as $CO_3^{2-}$, $PO_{4-}$, and $SO_4^{2-}$), about 0.04 wt % of amino acids (valine, arginine, methionine, etc.), about 0.66 wt % of other components (microorganisms, $Fe^{2+}$, $Cu^{2+}$, carbohydrate, etc.), and about 93.78 wt % of water.

(Microbial Cells Removal Step)

Microbial cells were removed from the first fermentation solution (concentration of quinolinic acid: 39 g/L, pH 5.6) by using a membrane filter (cartridge type, Pellicon 2, available from Millipore). The membrane filter had a pore size of about 0.1 m and a membrane area of about 0.5 $m^2$.

(Impurity Removal Step)

2.0 g of activated carbon was added to 930 mL of the first fermentation solution (concentration of quinolinic acid: 36 g/L) from which the microbial cells were removed, and stirred at about 80☐ for about 1 hour, followed by removing the activated carbon and insoluble materials through a vacuum filter (filter pore size: 0.7 μm).

(Concentration Step)

Water was removed from 915 mL of the first fermentation solution from which impurities were removed, by using a rotary evaporator at about 50☐ for about 3 hours to concentrate a concentration of quinolinic acid to about 120 g/L.

(Acidic Composition Preparation Step)

18 g of a 98%-conc. sulfuric acid was slowly added to 275 mL of the concentrated fermentation solution to prepare an acidic composition having a pH of 1.5, followed by stirring at about 20☐ for about 3 hours.

(Crystal Recovery Step)

Precipitated crystals of quinolinic acid in the acidic composition were separated using a vacuum filter (filter pore size: 8 μm), followed by cleaning the crystals with 80 g of deionized water, and drying in a 60☐-oven for about 3 hours.

The yield and purity of the recovered crystals of quinolinic acid are shown in Table 1.

Example 2

Quinolinic acid was refined in the same manner as in Example 1, except that the pH of the acidic composition was changed to 2.0, and the concentrated concentration of quinolinic acid in the concentration step was about 120 g/L.

Example 3

Quinolinic acid was refined in the same manner as in Example 1, except that the pH of the acidic composition was changed to 2.5, and the concentrated concentration of quinolinic acid in the concentration step was about 120 g/L.

Example 4

Quinolinic acid was refined in the same manner as in Example 1, except that the pH of the acidic composition was changed to 3.0, and the concentrated concentration of quinolinic acid in the concentration step was about 150g/L.

Example 5

Refining Method Including Recrystallization Step (Fermentation Solution Preparation Step)
A second fermentation solution (available from the CJ Cheil Jedang Bioscience R&D center) was prepared. The prepared second fermentation solution included about 4.00 wt % of quinolinic acid, about 0.43 wt % of organic acids (lactic acid, succinic acid, formic acid, acetic acid, etc.), about 1.38 wt % of ions (cations such as $Na^+$, $Mg^{2+}$, $NH^4$, and $K^+$, and anions such as $CO_3^{2-}$, $PO_4{}_-$, and $SO_4^{2-}$), about 0.05 wt % of amino acids (valine, arginine, methionine, etc.), about 1.42 wt % of other components (microorganisms, $Fe^{2+}$, $Cu^{2+}$, carbohydrate, etc.), and about 92.72 wt % of water.

(Microbial Cells Removal Step)
Microbial cells were removed from the second fermentation solution (concentration of quinolinic acid: 42 g/L, pH 5.6) by using a membrane filter (cartridge type, Pellicon 2, available from Millipore). The membrane filter had a pore size of about 0.1 μm and a membrane area of about 0.5 $m^2$.

(Impurity Removal Step)
1.5 g of activated carbon was added to 1160 mL of the second fermentation solution (concentration of quinolinic acid: 39 g/L) from which the microbial cells were removed, and stirred at about 80° C. for about 1 hour, followed by removing the activated carbon and insoluble materials through a vacuum filter (filter pore size: 0.7 μm).

(Concentration Step)
760 g of water was removed from 1060 mL of the second fermentation solution from which impurities were removed, by using a rotary evaporator at about 50° C. for about 3 hours to concentrate the second fermentation solution.

(Acidic Composition Preparation Step)
22 g of a 98%-conc. sulfuric acid was slowly added to 254 mL of the concentrated second fermentation solution to prepare an acidic composition having a pH of 1.5, followed by stirring at about 20° C. for about 3 hours.

(Crystal Recovery Step)
Precipitated crystals of quinolinic acid in the acidic composition were separated using a vacuum filter (filter pore size: 8 μm), followed by cleaning the crystals with 80 g of deionized water and drying in a 60° C.-oven for about 3 hours to obtain 40.26 g of crystals of quinolinic acid.

The recovered crystals were dissolved in deionized water and analyzed by high-performance liquid chromatography (HPLC). As a result, the purity of the crystals of quinolinic acid was about 95.3%.

(Recrystallization Step)
30 g of the recovered crystals of quinolinic acid was suspended in 320 mL of deionized water, and 10 mL of a 28%-ammonia water ($NH_4OH$) was added thereto to obtain a basic solution, followed by completely dissolving the crystals of quinolinic acid in the basis solution (Step of dissolving crystals in basic solution).

1.6 g of activated carbon was added to the basic solution, and stirred at about 70° C. for about 1 hour, followed by removing the activated carbon through a vacuum filter (filter pore size: 0.7 μm) (Impurity removal step).

18.4 g of a 98%-conc. sulfuric acid was slowly added to 314 mL of the basic solution from which the activated carbon was removed, to prepare an acidic composition having a pH of 1.0, followed by stirring at about 20° C. for about 3 hours (Acidic composition preparation step).

Precipitated crystals of quinolinic acid in the acidic composition were separated using a vacuum filter (filter pore size: 8 μm), followed by cleaning the crystals with 30 g of deionized water, and drying in a 60° C.-oven for about 3 hours to obtain 26.5 g of crystals of quinolinic acid (Crystal recovery step).

Example 6

Refining Method Including Recrystallization Step (Fermentation Solution Preparation Step)
A second fermentation solution (available from the CJ Cheil Jedang Bioscience R&D center) as used in Example 5 was prepared.

(Microbial Cells Removal Step)
Microbial cells were removed from the second fermentation solution (concentration of quinolinic acid: 42 g/L, pH 5.6) by using a membrane filter (cartridge type, Pellicon 2, available from Millipore). The membrane filter had a pore size of about 0.1 μm and a membrane area of about 0.5 $m^2$.

(Impurity Removal Step)
1.5 g of activated carbon was added to 1750 mL of the second fermentation solution (concentration of quinolinic acid: 39 g/L) from which the microbial cells were removed, and stirred at about 80° C. for about 1 hour, followed by removing the activated carbon and insoluble materials through a vacuum filter (filter pore size: 0.7 μm).

(Concentration Step)
1380 g of water was removed from 1730 mL of the second fermentation solution from which impurities were removed, by using a rotary evaporator at about 50° C. for about 3 hours to concentrate the second fermentation solution.

(Acidic Composition Preparation Step)
65 g of a 98%-conc. sulfuric acid was slowly added to 378 mL of the concentrated second fermentation solution to prepare an acidic composition having a pH of 2.0, followed by stirring at about 20° C. for about 3 hours.

(Crystal Recovery Step)
Precipitated crystals of quinolinic acid in the acidic composition were separated using a vacuum filter (filter pore size: 8 μm), followed by cleaning the crystals with 80 g of deionized water and drying in a 60° C.-oven for about 3 hours to obtain 57.6 g of crystals of quinolinic acid.

The recovered crystals were dissolved in deionized water and analyzed by HPLC. As a result, the purity of the crystals of quinolinic acid was about 93.9%.

(Recrystallization Step)
54.5 g of the recovered crystals of quinolinic acid was suspended in 900 mL of deionized water, and 20 g of a 28%-ammonia water ($NH_4OH$) was added thereto to obtain a basic solution, followed by completely dissolving the crystals of quinolinic acid in the basis solution (Step of dissolving crystals in basic solution).

2.73 g of activated carbon was added to the basic solution, and stirred at about 70° C. for about 1 hour, followed by removing the activated carbon through a vacuum filter (filter pore size: 0.7 μm) (Impurity removal step).

20.86 g of a 98%-conc. sulfuric acid was slowly added to 910 mL of the basic solution from which the activated carbon was removed, to prepare an acidic composition having a pH of 1.8, followed by stirring at about 20° C. for about 3 hours (Acidic composition preparation step).

785 g of water was removed from the acidic composition by using a rotary evaporator at about 50□ for about 3 hours (Concentration step).

Precipitated crystals of quinolinic acid in the concentrated acidic composition were separated using a vacuum filter (filter pore size: 8 μm), followed by cleaning the crystals with 12 g of deionized water and drying in a 60° C.-oven for about 3 hours to obtain 48.5 g of crystals of quinolinic acid (Crystal recovery step).

Comparative Example 1

Quinolinic acid was refined in the same manner as in Example 1, except that the pH of the acidic composition was changed to 4.0, and the concentrated concentration of quinolinic acid in the concentration step was about 400 g/L.

Evaluation Example 1

Evaluation of solubility of Quinolinic Acid with Respect to pH

Solubility of quinolinic acid in water at room temperature (about 23° C.) with respect to pH was evaluated using a pure quinolinic acid reagent (Sigma-Aldrich Prod. No. P63204), wherein the pH was controlled using a 28%-ammonia water and 98% sulfuric acid). The results are shown in FIG. 1

Figure 1:
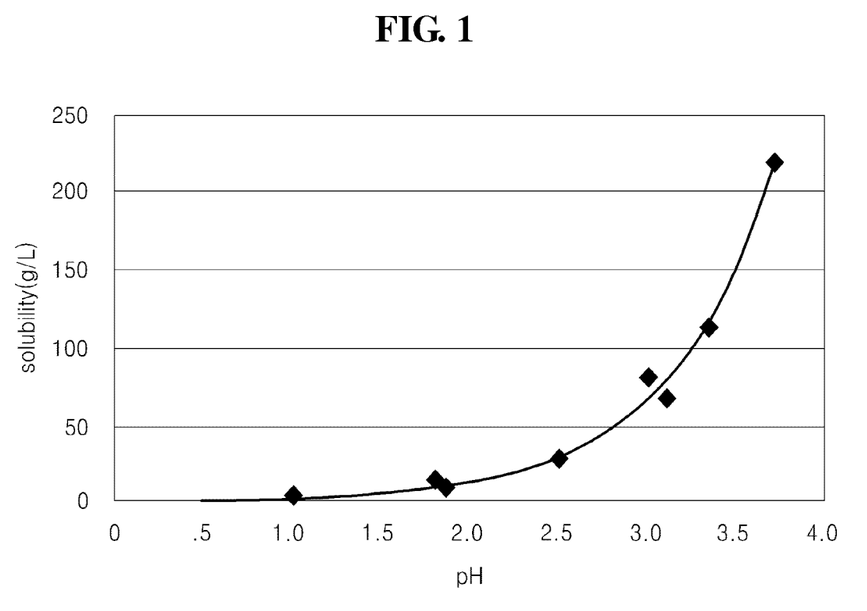
FIG. 1 is a graph of solubility of quinolinic acid with respect to pH.

Referring to FIG. 1, the lower the pH, the lower the solubility of quinolinic acid.

Evaluation Example 2

Evaluation of Yield and Purity of Crystals with Respect to pH of Acidic Composition The yields and purities of the crystals of linolinic acid obtained in Examples 1 to 6 and Comparative Example 1 are shown in Table 1.

TABLE 1

| Example | pH of acidic composition | Yield of crystals [%] | Purity of crystals [%] |
|---|---|---|---|
| Example 1 | 1.5 | 88 | 99.2 |
| Example 2 | 2.0 | 86 | 98.1 |
| Example 3 | 2.5 | 73 | 98.8 |
| Example 4 | 3.0 | 54 | 93.2 |
| Example 5 | 1.5/1.0 | 89/89 | 99.7 |
| Example 6 | 2.0/1.8 | 85/89 | 99.8 |
| Comparative Example 1 | 4.0 | 45 | 54.2 |

Referring to Table 1, the crystals of quinolinic acid of Examples 1 to 6 prepared using an acidic composition having a pH of about 3.5 or less were found to have improved yields and purities, compared to the crystals of quinolinic acid of Comparative Example 1.

INDUSTRIAL APPLICABILITY

As described above, according to the one or more embodiments, quinolinic acid may be refined through a comparatively simple process via adding an acid to a fermentation solution including quinolinic acid. High-purity quinolinic acid may be obtained with a high yield by recirculating a mother solution resulting from acid treatment and crystal separation acid treatment.

The invention claimed is:

1. A method of refining quinolinic acid, the method comprising:
   preparing a fermentation solution including at least one of quinolinic acid and a salt of thereof;
   removing microbial cells from the fermentation solution;
   preparing an acidic composition including at least one of quinolinic acid and a salt of thereof at a saturation concentration or more by adding an acid to the fermentation solution from which the microbial cells were removed; and
   recovering crystals of the at least one of quinolinic acid and a salt of thereof from the acidic composition.

2. The method of claim 1, wherein the acidic composition has a pH of about 3.5 or less.

3. The method of claim 1, wherein the acidic composition has a pH of about 1.0 to about 2.5.

4. The method of claim 1, wherein, in the preparing of the acidic composition, the acidic composition has a temperature of about 40° C. or less.

5. The method of claim 1, wherein the acid comprises at least one selected from sulfuric acid, hydrochloric acid, nitric acid, bromic acid (HBr), phosphoric acid ($H_3PO_4$), perchloric acid ($HClO_4$), and a mixture thereof.

6. The method of claim 1, further comprising, before the preparing of the acidic composition, removing impurities from the fermentation solution.

7. The method of claim 1, further comprising, before the preparing of the acidic composition, concentrating the fermentation solution.

8. The method of claim 1, further comprising, after the preparing of the acidic composition, concentrating the acidic composition.

9. The method of claim 1, further comprising, after the preparing of the acidic composition, cooling the acidic composition.

10. The method of claim 1, further comprising, after the preparing of the acidic composition, adding quinolinic acid crystal seeds to the acidic composition.

11. The method of claim 1, further comprising, after the recovering of the crystals, recrystallizing the recovered crystals.

12. The method of claim 11, wherein the recovering of the crystals comprises separating the crystals from the acidic composition.

13. The method of claim 11, wherein the recovering of the crystals further comprises cleaning and drying the separated crystals.

14. The method of claim 1, wherein a mother solution, obtained from the recovering of crystals, is recirculated into the fermentation solution.

15. The method of claim 11, wherein the recrystallizing of the recovered crystals comprises:

dissolving the recovered crystals in a basic solution;
preparing an acidic composition including at least one of quinolinic acid and a salt thereof at a saturation concentration or more by adding an acid to the basic solution; and
recovering crystals of the at least one of quinolinic acid and a salt thereof from the acidic composition.

16. The method of claim 15, wherein the basic solution comprises at least one selected from the group consisting of calcium hydroxide, magnesium hydroxide, calcium carbonate, ammonium hydroxide, sodium hydroxide, barium hydroxide. magnesium carbonate, and a mixture thereof.

17. The method of claim 15, wherein the recovering of the crystals comprises separating the crystals from the acidic composition.

18. The method of claim 15, wherein the recovering of the crystals further comprises cleaning and drying the separated crystals.

19. The method of claim 15, wherein a mother solution, obtained from the recovering of the crystals, is recirculated into the fermentation solution.

* * * * *